United States Patent
De Vecchi et al.

(10) Patent No.: US 11,987,808 B2
(45) Date of Patent: May 21, 2024

(54) METHOD OF HUMAN PERIFERIC SENSORY NEURONS DIFFERENCIATION FROM HUMAN STEM CELLS AND USES THEREOF

(71) Applicant: L'OREAL, Paris (FR)

(72) Inventors: Rodrigo De Vecchi, Rio de Janeiro (BR); Stevens Kastrup Rehen, Rio de Janeiro (BR); Marilia Zaluar, Rio de Janeiro (BR); Lionel Breton, Aulnay-sous-bois (FR)

(73) Assignee: L'OREAL, Paris (FR)

( * ) Notice: Subject to any disclaimer, the term of this patent is extended or adjusted under 35 U.S.C. 154(b) by 652 days.

(21) Appl. No.: 16/624,663

(22) PCT Filed: Jun. 20, 2017

(86) PCT No.: PCT/BR2017/050157
§ 371 (c)(1),
(2) Date: Dec. 19, 2019

(87) PCT Pub. No.: WO2018/232476
PCT Pub. Date: Dec. 27, 2018

(65) Prior Publication Data
US 2020/0216803 A1    Jul. 9, 2020

(51) Int. Cl.
*C12N 5/0793* (2010.01)

(52) U.S. Cl.
CPC .......... *C12N 5/062* (2013.01); *C12N 2500/38* (2013.01); *C12N 2501/01* (2013.01); *C12N 2501/11* (2013.01); *C12N 2501/115* (2013.01); *C12N 2501/13* (2013.01); *C12N 2501/15* (2013.01); *C12N 2501/155* (2013.01); *C12N 2502/094* (2013.01); *C12N 2506/45* (2013.01)

(58) Field of Classification Search
CPC ................ C12N 5/062; C12N 2500/38; C12N 2501/01; C12N 2501/11; C12N 2501/115; C12N 2501/13; C12N 2501/15; C12N 2501/155; C12N 2502/094; C12N 2506/45
See application file for complete search history.

(56) References Cited

U.S. PATENT DOCUMENTS

| 9,511,011 B2 | 12/2016 | Chung et al. | |
| 2013/0183674 A1* | 7/2013 | Studer ................ | G01N 33/5058 435/7.1 |
| 2016/0201032 A1 | 7/2016 | Studer et al. | |

FOREIGN PATENT DOCUMENTS

| AU | 2015203079 A1 | 7/2015 |
| JP | 5904789 B2 * | 4/2016 |

OTHER PUBLICATIONS

Kumamoto et al ("Coculture system of keratinocytes and dorsal-root-ganglion-derivedcells for screening neurotrophic factors involved in guidance of neuronal axon growth in the skin," Experimental Dermatology, 2014,23, 58-77) (Year: 2014).*
JP2013-135637—Eng Language Machine Translation of JP 5904789-B2 (Year: 2013).*
Jones et al ("Development and validation of an in vitro model system to study peripheral sensory neuron development and injury," Scientific Reports | (2018) 8:15961) (Year: 2018).*
Hombach-Klonisch ("Adult stem cells and their trans-differentiation potential—perspectives and therapeutic applications," J Mol Med (2008) 86:1301-1314) (Year: 2008).*
Wattanapanitch et al ("Dual Small-Molecule Targeting of SMAD Signaling Stimulates Human Induced Pluripotent Stem Cells toward Neural Lineages," PLoS ONE 9(9): e106952 (2014)), (Year: 2014).*
Hall BK, et al. Effects of growth factors on the differentiation of neural crest cells and neural crest cell-derivatives. Int J Dev Biol. Dec. 1, 1991;35(4):367-387. (Year: 1991).*
Fukuta M, et al. Derivation of mesenchymal stromal cells from pluripotent stem cells through a neural crest lineage using small molecule compounds with defined media. PLoS One. Dec. 2, 2014;9(12):e112291. doi: 10.1371/journal.pone.0112291 (Year: 2014).*
Singha et al. Divergent effects of Smad2 and Smad3 onTGF-β mediated breast cancer cell growth and expression ofTMEPAI/PMEPA1. Cancer Res, Aug. 1, 2015; 75(15): 1947; cited p. 1-2 (Year: 2015).*
Wongpaiboonwattana W, Stavridis MP. Neural differentiation of mouse embryonic stem cells in serum-free monolayer culture. J Vis Exp. May 14, 2015;(99):e52823. doi:10.3791/52823 (Year: 2015).*
Rharass T, et al. Ascorbic acid alters cell fate commitment of human neural progenitors in a WNT/β-catenin/ROS signaling dependent manner. J Biomed Sci. Oct. 16, 2017;24(1):78. Published Oct. 16, 2017. doi:10.1186/s12929-017-0385-1 (Year: 2017).*
Stuart M. Chambers et al: "Combined small-molecule inhibition accelerates developmental timing and converts human pluripotent stem cells into nociceptors", Nature Biotechnology, vol. 30, No. 7, Jul. 1, 2012 (Jul. 1, 2012), pp. 715-720.

(Continued)

*Primary Examiner* — Titilayo Moloye
*Assistant Examiner* — Gillian C. Reglas
(74) *Attorney, Agent, or Firm* — McNees Wallace & Nurick LLC

(57) ABSTRACT

The present invention relates to the field of stem cell biology, in particular the linage specific differentiation of pluripotent or multipotent stem cells. Specifically described are methods to direct the lineage specific differentiation of hiPSC to sensitive neurons or neuronal fibers innervating the human skin, such as neural crest stem cells (NCPCs) and here called peripheral sensory neurons (PSNs) using novel culture conditions. It is also described a method for screening a biological agent in vitro. The PSNs obtained using the methods of the present invention are further contemplated for various uses including, but limited to, use in in vitro tests or disease modelling, such as drug discovery assays, cell therapy on a higher scale, detecting a range of skin irritants and other compounds of interest, for studying skin aging mechanism, and for producing a dermocosmetic product. Also, it is contemplated the use of ligands in vitro for checking the differentiation and/or activation of the PSN cells, produced by the method of the invention, and the PSN cells, produced by the method of the invention.

10 Claims, 5 Drawing Sheets

(56) References Cited

OTHER PUBLICATIONS

Gareth T. Young et al: "Characterizing Human Stem Cell-derived Sensory Neurons at the Single-cell Level Reveals Their Ion Channel Expression and Utility in Pain Research", Molecular Therapy, vol. 22, No. 8, Aug. 1, 2014 (Aug. 1, 2014), pp. 1530-1543.
Katherine S. Lee et al: "Human Sensory Neurons Derived from Induced Pluripotent Stem Cells Support Varicella-Zoster Virus Infection", Plos One, vol. 7, No. 12, Dec. 28, 2012 (Dec. 28, 2012), p. e53010.
Pomp O. et al: "Generation of Peripheral Sensory and Sympathetic Neurons and Neural Crest Cells from Human Embryonic Stem Cells", Stem CE, Alphamed Press, Dayton, OH, US, vol. 23, No. 7, Aug. 1, 2005 (Aug. 1, 2005), pp. 923-930.
PCT International Search Report for PCT/BR2017/050157 dated Feb. 10, 2017.

\* cited by examiner

METHOD OF HUMAN PERIFERIC SENSORY NEURONS DIFFERENCIATION FROM HUMAN STEM CELLS AND USES THEREOF

FIELD OF THE INVENTION

The present invention relates to the field of stem cell biology, in particular the linage specific differentiation of pluripotent or multipotent stem cells, which can include, but is not limited to, human embryonic stem cells (hESC), human induced pluripotent stem cells (hiPSC), somatic stem cells, cancer stem cells, or any other cell capable of lineage specific differentiation. Specifically described are methods to direct the lineage specific differentiation of hiPSC to sensitive neurons or neuronal fibers innervating the human skin, such as neural crest stem cells (NCPCs) and here called peripheral sensory neurons (PSNs) using novel culture conditions. The PSNs made using the methods of the present invention are further contemplated for various uses including, but not limited to, use in vitro drug discovery assays, and cell therapies. Moreover, this method can be applied to patient-derived hiPSCs and thus serve as a powerful tool to model human diseases.

BACKGROUND OF THE INVENTION

The cellular microenvironment (composed of soluble signals, insoluble/physical signals and cell-cell interactions) plays a decisive role in regulating stem cell differentiation. However, the function of stem cell micro-environmental factors on differentiation is extremely difficult to investigate since these studies require extensive knowledge of multiple regulatory signals and how they interact to influence cellular function. While generous progress has been made as an attempt to address these concerns, the conventional methods currently available for such an investigation are still limited.

Embryonic and somatic stem cells have the ability to differentiate into any cell type, for example, human induced pluripotent stem cells (hiPSCs) are being used to generate different neuronal types to study their biology, pharmacology and to screen for potential new drugs.

The hiPSCs may differentiate into neural crest precursor cells (NCPCs), which in turn, differentiate into various cell types and tissues during embryonic development including smooth muscles, connective tissue, bone, cartilage, fat, endocrine cells, melanocytes, neurons and glia, amongst many others. The high potential of NCPCs to differentiate into peripheral sensory neurons (PSN) turns these cells into a powerful tool to investigate various somatosensory disorders and a reliable model for drug screening, not only to pain researchers and chemists aiming for new analgesics, but also to the cosmetic industry to substitute certain animal tests, such as skin irritation, and skin aging. Nevertheless, the in vitro derivation of neurons from hiPSCs requires extended culture periods typically lasting 30 days or more.

There have been only few studies addressing the generation of NCSCs and PSNs from either Embryonic Stem Cells (ESCs) or human induced Pluripotent Stem Cells (hiPSCs). Most of these studies were based on murine stromal cells and co-culture, which promotes neural differentiation of stem cells and formation of neural rosettes or neurospheres. Cell type heterogeneity is one of the main obstacles in those culture systems, besides differentiation yield and neurons functionality. Recent studies tried to overcome these issues. However, the results generated costly or time-consuming protocols and low efficiency in generating NCPCs or mature PSNs.

Also, there have been several attempts to develop efficacious stem cell differentiation protocol to obtain peripheral neurons in vitro.

In 2012, Chambers et al. (Combined small-molecule inhibition accelerates developmental timing and converts human pluripotent stem cells into nociceptors. *Nat Biotechnol* 2012; 30:715-720) applied a combinatorial small molecule-based approach to identify necessary factors to produce nociceptors, such as human β-nerve growth factor (NGF), brain-derived neurotrophic factor (BDNF) and glial cell-derived neurotrophic factor (GDNF).

Other attempts ensued optimizing even further the differentiation protocol and were able to show expression of canonical peripheral markers, such as BRN3A, peripherin, and TUJ1 in hPSC-derived sensory neurons. The expression of the capsaicin receptor (TRPV1) revealed that the majority of TUJ1-positive cells harbored nociceptor identity, with 83% of TUJ1-positive cells within ganglion-like clusters positive for TRPV1. Functional analysis tested the neuronal excitability by whole-cell patch-clamp experiments, showing that hiPSC-derived nociceptors fired tonically or phasically, when electronically evoked (Eberhardt et al., Pattern of Functional TTX-Resistant Sodium Channels Reveals a Developmental Stage of Human iPSC- and ESC-Derived Nociceptors. Stem Cell Reports Journal Vol. 5 j 305-313 j, 2015). TRPV1/TRPA1 channel expression has been shown in a wide variety of tissues but evidence of functionality has not yet been demonstrated for all of these receptors (Fernandes et al., The functions of TRPA1 and TRPV1: moving away from sensory nerves. British Journal of Pharmacology. 2012; 166(2):510-521).

One of the first cell types in which functionality was first identified in epidermal keratinocytes (Inoue et al. Functional vanilloid receptors in cultured normal human epidermal keratinocytes. Biochem Biophys Res Commun. 2002; 291: 124-129.) demonstrated that both capsaicin and acidification produced elevations in the intracellular calcium concentration in cultured human epidermal keratinocytes. Furthermore, these increases were inhibited by the TRPV1 antagonist, capsazepine (Inoue et al., 2002). Similarly, treatment of human skin fibroblasts with capsaicin induced significant changes in the membrane current and the intracellular calcium level that were antagonized by capsazepine (Kim et al., Expression of vanilloid receptor 1 in cultured fibroblast. Exp Dermatol. 2006; 15:362-367).

Kreitzer et al. (A robust method to derive functional neural crest cells from human pluripotent stem cells. Am J Stem Cells. 2013; 2(2):119-31) were able to differentiate multiple human pluripotent stem cell lines into neural crest (NC) cells. By initiating NC differentiation soon after neural precursor formation, they were able to generate high percentages of NC cells (80% on average, and as high as ~90% in some NC differentiations). These NC cells could proliferate, self-renew, migrate to appropriate cues, and spontaneously differentiate into various NC lineages and peripheral nerves, expressing the appropriate NC markers, including HNK1 and p75, in a total of 8 days, which is significantly faster than previously described protocols (Chambers et al., Highly efficient neural conversion of human ES and iPS cells by dual inhibition of SMAD signaling. Nat. Biotechnol. 27, 275-280 (2009); Menendez et al., Directed differentiation of human pluripotent cells to neural crest stem cells. Nature Protoc. 2013; 8: 203-212; Lee et al., Human Sensory Neurons Derived from Induced Pluripotent Stem Cells Support Varicella-Zoster Virus Infection. PLoS ONE 7(12): e53010).

In 2014, Young and colleagues (Characterizing human stem cell-derived sensory neurons at the single-cell level reveals their ion channel expression and utility in pain research. Mol. Ther. 2014; 22, 1530-1543) reported an optimized protocol for the generation of sensory neurons from human embryonic stem cells via small-molecule inhibition, being able to generate a highly enriched population of sensory neurons that expressed more than 80% of the ion channels found in adult human dorsal root ganglia (DRG). Stem cells were grown on matrigel and treated with medium containing a number of small-molecule drugs driving differentiation toward a neuronal fate for 10 days. Many individual cells examined expressed markers indicative of DRG as early as 16 days of differentiation. However, it is also evident from this analysis that the cell population at day 16 remained heterogeneous (Young et al., Characterizing human stem cell-derived sensory neurons at the single-cell level reveals their ion channel expression and utility in pain research. Mol. Ther. 2014; 22, 1530-1543).

In accordance with the aforementioned, there have been several attempts to develop efficacious stem cell differentiation protocols to obtain peripheral neuron in vitro, however, there is still a need for an improved method to produce peripheral sensory neurons, with increased purity (homogeneity), yield, and/or neurons functionality.

SUMMARY OF THE INVENTION

The present invention discloses a new and effective lineage-specific method for differentiating hiPSCs into sensitive neurons or neuronal fibers innervating the human skin, such as neural crest progenitor cells (NCPCs) and peripheral sensorial neurons (PSNs), with a high differentiation yield as well as less labor intensive, less prone to errors and more robust and reproducible.

Thus, a first object of the present invention is a method for inducing differentiation to peripheral sensory neural (PSN) cells, comprising the steps of:
- (a) the provision of:
  - (i) a cell culture comprising human stem cells;
  - (ii) a 3N medium;
  - (iii) at least one SMAD pathway inhibitor;
- (b) contacting said stem cell of (i) with (ii) and (iii) on a first culture vessel 2 to 22 days in vitro;
- (c) contacting in a second culture vessel the primarily differentiated cells with 3N medium, supplemented with at least one mitogen, coated with polyornithine/laminin, wherein the primarily differentiated cells are maintained in said culture for up to 12 days;
- (d) contacting the primarily differentiated cells with 3N medium, supplemented with at least one neurotrophic factor, at least one differentiation inductor and at least one cell transduction inductor, maintaining the primarily differentiated cells for 5 to 25 days in culture for obtaining the secondary differentiated cells;
- (e) culturing the secondary differentiated cells from 2 to 22 days in conditioned medium from human epidermal keratinocytes, neonatal (HEKn).

In a preferred embodiment of the method of the invention, the human stem cell is a human induced pluripotent stem cell (hiPSC).

Preferably, the SMAD pathway inhibitors are chosen from LDN193189, SB431542 and CHIR, or any mixture thereof, in that, preferably, the LDN193189 is between about 100 and about 700 nM, the SB431542 is between about 0.1 and about 100 µM and the CHIR is between about 0.1 and about 10 µM.

Also according to a preferred embodiment of the method of the present invention, the primarily differentiated cells are Neural Crest Progenitor Cells (NCPC), in that, preferably, the NCPCs express one or more markers selected from the group consisting of Nestin, TRPV1, Peripherin, Pax 6 and BRN3a.

Preferably, the mitogens are chosen from fibroblast growth factors (such as FGF-2) and EGF, or any mixture thereof.

Preferably, the neurotrophic factor is chosen from brain derived neurotrophic factor (BDNF), glial cell line derived neurotrophic factor (GDNF), NT-3, nerve growth factor (NGF) or any mixture thereof.

Preferably, the differentiation inductor is chosen from ascorbic acid.

Preferably, the cell transduction inductor is chosen from cyclic adenosine monophosphate (cAMP).

Preferably, the secondary differentiated cells are peripheral sensory neuronal (PSN) cells.

Preferably, the peripheral sensory neurons express one or more markers selected from the group consisting of TRPV1 and Substance P.

A second object of the present invention is a method of screening a biological agent in vitro, comprising:
- (a) the provision of:
  - (i) a peripheral sensory neurons derived in vitro from a method for inducing differentiation to peripheral sensory neuronal (PSN) cells, as defined in the present application;
  - (ii) a test compound; and
- (b) contacting said peripheral sensory neurons with said test compound and measuring the peripheral sensory neurons function, wherein said function is measurement of at least one marker's activity.

In a preferred embodiment of the second object of the present invention, the peripheral sensory neurons are derived from human induced pluripotent stem cells (hiPSC).

Preferably, the marker is chosen from TRPV1 and Substance P.

A third object of the present invention is the use of peripheral sensory neurons (PSNs), produced by the method for inducing differentiation to peripheral sensory neuronal (PSN) cells, as defined in the present invention, for performing in vitro tests, wherein, according to a preferred embodiment of the present invention, the in vitro test is detecting a range of skin irritants, allergens, anti-aging, skin soothing and/or anti-inflammatories.

Preferably, the irritants are chosen from fragrances, preservatives, solvents, propellants, as exfoliants and skin cell renewal agents, anti-acne drugs, antiperspirant compounds, antihistamines, anti-inflammatory agents, skin protective agents, insect repellent chemicals, sunscreens, surfactants, preservatives, skin soothing agents, anti-aging drugs, wound healing drugs, topical biological compounds used in cosmetics and/or dermocosmetics, or any mixture thereof.

Also according to a preferred embodiment of the present invention, the in vitro test is studying skin aging mechanism.

A fifth object of the present invention is the use of ligands in vitro, for checking the differentiation and/or activation of the cell, produced by the method for inducing differentiation to peripheral sensory neuronal (PSN) cells, as defined in the present invention.

Preferably, the differentiation and/or activation of the cell is checked by analyzing the TRPV1 activity and/or substance P releasing.

Preferably, the ligands are selected from anandamide, capsaicin, resiniferotixin, red ruthenium, lidocaine, myricitrin, chronic capsaicin, camphor, riamiloride, capsazepine, linopirdine and/or rimonabant.

A sixth object of the present invention is the use of peripheral sensory neurons (PSNs) cells, produced by the method for inducing differentiation to peripheral sensory neuronal (PSN) cells, as defined in the present invention, for producing a cosmetic product.

A seventh object of the present invention is the peripheral sensory neuronal (PSN) cells, produced by the method for inducing differentiation to peripheral sensory neuronal (PSN) cells, as defined in the present invention.

DETAILED DESCRIPTION OF THE INVENTION

Figure 1:
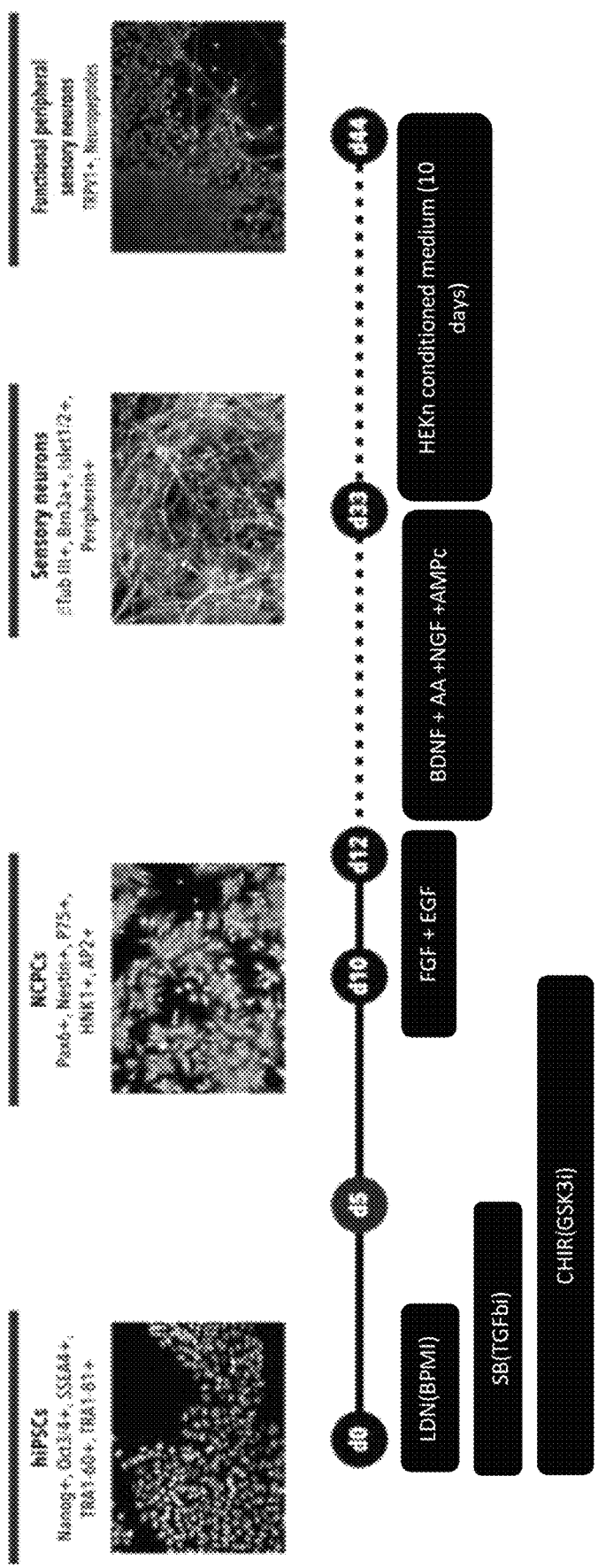
FIG. 1 shows Peripheral sensory neurons differentiation steps time course. Schematic model of the differentiation protocol into sensory neurons. Day 0 (D0): differentiation starts with hiPS cells presenting all main pluripotency markers; D5: formation of neural tube-like structures; D10: cell commitment to NCPC phenotype; D13: replacement to media supplemented with brain derived neurotrophic factor (BDNF), ascorbic acid (AA), glial derived neurotrophic factor (GDNF), neurotrophin 3 (NT-3) and cyclic AMP (cAMP) to induce NCPC differentiation into sensory neurons; D13-D33: maturation of sensory neurons.

Neural crest precursor cells (NCPCs) differentiate into various cell types and tissues during embryonic development including smooth muscles, connective tissue, bone, cartilage, fat, endocrine cells, melanocytes, neurons and glia, amongst many others. The high potential of NCPCs to differentiate into peripheral sensory neurons (PSN) turns these cells into a powerful tool to investigate various somatosensory disorders and a reliable model for drug/irritants screening but the in vitro derivation of neurons from hiPSCs requires extended culture periods typically lasting 30 days or more. There have been only few studies addressing the generation of NCSCs and PSNs from either Embryonic Stem Cells (ESCs) or human induced Pluripotent Stem Cells (hiPSCs). Most of these studies were based on murine stromal cells and co-culture, which promotes neural differentiation of stem cells and formation of neural rosettes or neurospheres. Cell type heterogeneity is one of the main obstacles in those culture systems, besides differentiation yield and neurons functionality. Recent publications tried to overcome these issues, however, the results generated costly or time-consuming protocols and low efficiency in generating NCPCs or mature PSNs.

In view of the above, while generous progress has been made as an attempt to address these concerns, the conventional methods currently available for such an investigation are still limited. Therefore, it is still necessary the development of a method for inducing differentiation of hiPSCs into PSNs resulting in homogeneous culture systems, presenting differentiation yield and neurons functionality, especially focused on drug discovery assays and the substitution of certain animal tests in the cosmetic industry.

The present invention relates to an efficient method for inducing differentiation of a lineage-specific stem cell, particularly from hiPSCs into sensitive neurons or neuronal fibers innervating the human skin, such as neural crest stem cells (NCPCs) and peripheral sensory neurons (PSNs), with a high differentiation yield, and uses of a differentiated cell produced by the method of the present invention for detecting a range of skin irritants and for studying skin aging mechanism. More specifically, the present invention provides a method to differentiate hiPSCs into neural crest progenitor cells (NCPCs) via treatment with Smad inhibitors, from 2 to 22 days, preferably from 5 to 18 days, more preferably from 7 to 12, even more preferably 12 days.

The primarily differentiated cells are contacted with 3N medium, supplemented with at least one mitogen, coated with polyornithine/laminin, and may be maintained in said culture for up to 12 days, preferably from 2 to 10, more preferably for 2 days. Subsequently, the primarily differentiated cells are contacted with 3N medium, supplemented with at least one neurotrophic factor, at least one differentiation inductor and at least one cell transduction inductor, in that the primarily differentiated cells are maintained in culture from 5 to 25 days, preferably from 10 to 20, more preferably 15 days, for obtaining the secondary differentiated cells. Then, culturing the secondary differentiated cells from 2 to 22 days, preferably 2 to 10 days, in medium conditioned with 50% to 100%, preferably with 60% to 90%, more preferably from 70% to 80%, even more preferably with 75% human epidermal keratinocytes neonatal (HEKn) medium.

Then a differentiation protocol to obtain peripheral sensory neurons from NCPC during up to 35 days. Functional tests were performed to prove neuronal activity and responsivity from day 11 after PSN differentiation. The data presented herein shows that the canonical Wnt signaling pathway plays an important role during neural crest cells differentiation, while the inhibition of BMP and Activin A/Nodal signaling pathways leads to an efficient and fast generation of NPCs.

The primary objective of this method was to avoid having to sort the p75/Hnk1+NPCs, since a high percentage of these cells was expected. The method of the present invention includes the BMP type I receptors ALK2 and ALK3-inhibitor LDN-193189 (LDN) to the differentiation protocol in which the Activin A/Nodal signaling blocker, SB431542 (SB), was used, in parallel with the GSK-3 inhibitor CHIR, resulting into a dual-Smad-inhibition condition. This method is simpler to execute and does not require a FACS sorting step, which means that it is significantly less labor intensive, less prone to errors and more robust and reproducible. Since then, induced NCPCs obtained using this method was used to differentiate into Peripheral Neurons by means of incubation with GDNF ligands and neurotrophins, followed by ten days in 75% conditioned medium from human epidermal keratinocytes, neonatal (HEKn). The neurons generated were functional in response to anandamide, which caused a release of substance P (SP). Calcium signals were modest in response to capsaicin and other agents and it was observed a further increase in the expression of PSN markers such as TRPV1 after conditioned medium treatment.

Also, a further embodiment of the present invention includes a method for screening a biological agent in vitro, comprising the steps as described.

Additionally, the PSNs made using the method of the present invention are further contemplated for various uses including, but limited to, use in in vitro tests, such as drug discovery assays, cell therapy on a higher scale, detecting a range of skin irritants and other compounds of interest, for studying skin aging mechanism, and for producing a cosmetic product, such as an antiaging skin product.

Also, it is contemplated the use of ligands in vitro for checking the differentiation and/or activation of the PSN cells, produced by the method of the invention, and the PSN cells, produced by the method of the invention.

Before the present invention is further described by means of the examples, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by a person skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

All of the methods disclosed and claimed herein can be made and executed without undue experimentation in light of the present disclosure. While the methods of this invention have been described in terms of preferred embodiments, it will be apparent to those skilled in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Unless otherwise disclosed, all technical terms, notations and other scientific terminology used herein are intended to have the meanings normally understood by those skilled in the art in the field of the present invention. In some cases, terms with commonly understood meanings are defined herein for the purpose of bringing clarity and/or prompt reference, and the inclusion of such definitions in this document is not necessarily to be interpreted as representing a substantial difference in the definitions generally understood in the prior art.

Definitions

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm, and ectoderm). Stem cells also give rise to tissues of multiple germ layers following transplantation and contribute substantially to most, if not all, tissues following injection into blastocysts. Stem cells are classified by their developmental potential.

As used herein, the term "totipotent" refers to an ability to give rise to all the cell types of the body plus all of the cell types that make up the extraembryonic tissues.

As used herein, the term "multipotent" refers to an ability to develop into more than one cell type of the body.

As used herein, the term "pluripotent" refers to an ability to develop into the three developmental germ layers of the organism including endoderm, mesoderm, and ectoderm.

Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, TRA-1-60, TRA- 1-81. In one embodiment, the pluripotent stem cells suitable for use in the methods of the invention express one or more of NANOG, SOX2, TRA-1-60 and TRA-1-81, and lack expression of a marker for differentiation neural markers Islett BRN3A, peripherin and TRPV1.

Human induced pluripotent stem cells (hiPSC), as used herein, refers to a stem cell induced from a somatic cell, e.g., a differentiated somatic cell, and that has a higher potency than said somatic cell. hiPS cells are capable of self-renewal and differentiation into mature cells, e.g., neural crest progenitor cells (NCPCs).

The NCPCs are also referred in the present invention as primarily differentiated cells.

As used herein, the terms "Peripheral sensory neuronal (PSN) progenitor cell" and "secondary differentiated cells" means a cell derived from a mammalian neural crest stem cell which is committed to one or more PNS neuronal lineages and is a dividing cell but does not yet express surface or intracellular markers found on more differentiated, non-dividing PSN neuronal cells. When these PSN neuronal progenitor cells are placed in appropriate culture conditions they differentiate into mature PSN neurons expressing the appropriate differentiation markers, for example, peripherin and TRPV (transient receptor potential).

"Cell culture" or "culturing" generally refer to cells taken from a living organism and grown under controlled conditions ("in culture" or "cultured"). A primary cell culture is a culture of cells, tissues, or organs taken directly from an organism before the first subculture. Cells are expanded in culture when they are placed in a growth medium under conditions that facilitate one or both of cell growth and division, resulting in a larger population of the cells. When cells are expanded in culture, the rate of cell proliferation is sometimes measured by the amount of time needed for the cells to double in number (referred to as doubling time).

A culture vessel used for culturing the stem cell(s) can include, but is particularly not limited to: flask, flask for tissue culture, dish, petri dish, dish for tissue culture, multi dish, micro culture vessel, micro-well plate, multi plate, multi-well plate, micro slide, chamber slide, schale, tube, tray, culture bag, and roller bottle, as long as it is capable of culturing the stem cells therein.

The culture vessel can be cellular adhesive or non-adhesive and selected depending on the purpose. The cellular adhesive culture vessel can be coated with any of substrates for cell adhesion such as extracellular matrix (ECM) to improve the adhesiveness of the vessel surface to the cells. The substrate for cell adhesion can be any material intended to attach stem cells or feeder cells (if used).

Culturing conditions can be appropriately defined. For example, the culturing temperature can be about 30 to 40° C. and preferably about 37° C. but particularly not limited to it. The $CO_2$ concentration can be about 1 to 10% and preferably about 2 to 5%. The oxygen tension can be 1-10%.

Differentiation is the process by which an unspecialized ("uncommitted") or less specialized cell acquires the features of a specialized cell such as, a nerve cell or a muscle cell. A differentiated cell or a differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type.

A suitable neural induction medium may be based on a standard medium which supports neural induction, neurogenesis and neuronal differentiation. A 3N medium may comprise a 1:1 mixture of N2-containing and B27 media-containing, wherein the N2-containing medium comprises DMEM/F12 supplemented with N2 (GIBCO), insulin, L-glutamine, non-essential amino acids (NEAA), b-mercaptoethanol, penicillin and Streptomycin and the B27-containing medium comprises neurobasal (Invitrogen) supplemented with B27 supplement (GIBCO), L-glutamine, penicillin and streptomycin.

The 3N medium described above may be supplemented with TGFβ and so BMP signaling inhibitors to produce a neural induction medium.

As used herein, the term "inhibitor", refers to a compound that reduces or abolishes the biological function or activity of the recited signaling pathway, by interfering with a specific target that is part of this signaling pathway or by interfering with the interaction between two or more targets. An inhibitor may perform any one or more of the following effects in order to reduce or abolish the biological function or activity of the protein to be inhibited: (i) the transcription of the gene encoding the protein to be inhibited is lowered, i.e. the level of mRNA is lowered, (ii) the translation of the mRNA encoding the protein to be inhibited is lowered, (iii) the protein performs its biochemical function with lowered efficiency in the presence of the inhibitor, and (iv) the protein performs its cellular function with lowered efficiency in the presence of the inhibitor.

Such compounds may include, without being limited to, small molecule, peptide, peptidomimetic, natural compound, siRNA, anti-sense nucleic acid, aptamer, or antibody. For example, in one embodiment of the present invention it may be used "small molecules" as inhibitors, such as an inhibitor of SMAD signaling.

In other words, an inhibitor is any compound or molecule that changes any activity of a named protein (signaling molecule, any molecule involved with the named signaling molecule, a named associated molecule, such as a glycogen synthase kinase 3β (GSK3β) (e.g., including, but not limited to, the signaling molecules described herein), for one example, via directly contacting SMAD signaling, contacting SMAD mRNA, causing conformational changes of SMAD, decreasing SMAD protein levels, or interfering with SMAD interactions with signaling partners (e.g., including those described herein), and affecting the expression of SMAD target genes (e.g. those described herein).

Inhibitors also include molecules that indirectly regulate SMAD biological activity by intercepting upstream signaling molecules (e.g. within the extracellular domain, examples of a signaling molecule and an effect include: Noggin which sequesters bone morphogenic proteins, inhibiting activation of ALK receptors 1,2,3, and 6, thus preventing downstream SMAD activation. Likewise, Chordin, Cerberus, Follistatin, similarly sequester extracellular activators of SMAD signaling. Bambi, a transmembrane protein, also acts as a pseudo-receptor to sequester extracellular TGFβ signaling molecules. Antibodies that block activins, nodal, TGFβ, and BMPs are contemplated for use to neutralize extracellular activators of SMAD signaling, and the like). Thus, in one embodiment, an inhibitor of the present inventions induces (changes) or alters differentiation from a default to a non-default cell type. In a preferred embodiment, an inhibitor of the present inventions "alters" or "lowers" or "blocks" default signaling in order to direct cellular differentiation towards a non-default cell type, such as described herein for producing peripheral sensory neurons cells of the present invention.

Thus, an inhibitor of the present invention is a natural compound or small molecule for modified signal molecule activity that assists in producing peripheral sensory neurons cells of the present invention. Inhibitors are described in terms of competitive inhibition (binds to the active site in a manner as to exclude or reduce the binding of another known binding compound) and allosteric inhibition (binds to a protein in a manner to change the protein conformation in a manner which interferes with binding of a compound to that protein's active site) in addition to inhibition induced by binding to and affecting a molecule upstream from the named signaling molecule that in turn causes inhibition of the named molecule. In some cases, an inhibitor is referred to as a "direct inhibitor" which refers to inhibiting a signaling target or a signaling target pathway by actually contacting the signaling target. Exemplary direct inhibitors include but are not limited to: lidocaine, myricitrin, chronic capsaicin, camphor, amiloride, capsazepine, linopirdine, and most local anesthetics that block general nerve function.

As used herein, the term "extracellular signaling influences" refers to the effect that extracellular signaling molecules (e.g., test agents such as small molecules described herein, pharmaceutical agents, ligands to a receptor, cytokines, chemokines, soluble factors, adhesion molecules, or other signaling molecules) have on a cell (e.g., a eukaryotic cell). In some embodiments, extracellular signaling reduces signaling activity, such as SMAD activity, alters SMAD activation kinetics, or alters SMAD target gene expression pattern.

As used herein, the term "Sma Mothers Against Decapentaplegic" or "Small Mothers Against Decapentaplegic" or "SMAD" refers to a signaling molecule.

As used herein, the term "SB431542" refers to a molecule capable of lowering or blocking transforming growth factor beta (TGFβ)/Activin-Nodal signaling with a number CAS 301836-41-9, a molecular formula of $C_{22}H_8N_4O_3$, and a name of 4-[4-(1,3-benzodioxol-5-yl)-5-(2-pyridinyl)-1H-imidazol-2-yl]-benzamide, for example, see structure below:

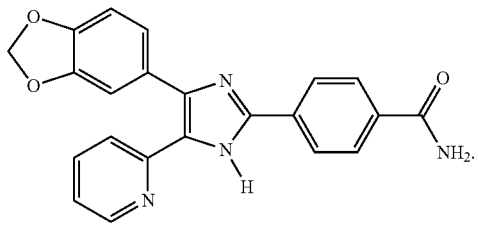 [SMILES: NC(=O)c1ccc(-c2nc(-c3ccc4c(c3)OCO4)c(-c3ccccn3)[nH]2)cc1]

Preferred amounts of SB431542 to be employed are between about 0.1 and about 100 μM, more preferably between about 1 and about 50 μM, such as for example between about 5 and about 20 μM and most preferably the amount is about 10 μM.

As used herein, the term "LDN193189" refers to a small molecule DM-3189, IUPAC name 4-(6-(4-(piperazin-1-yl)phenyl)pyrazolo[1,5-a]pyrimidin-3-yl)quinoline, with a chemical formula of $C_{25}H_{22}N_6$ and CAS number 1062368-24-4. The LDN193189 is capable of functioning as a SMAD signaling inhibitor. LDN193189 is also highly potent small-molecule inhibitor of ALK2, ALK3, and ALK6, protein tyrosine kinases (PTK), inhibiting signaling of members of the ALK1 and ALK3 families of type I TGFβ receptors, resulting in the inhibition of the transmission of multiple biological signals, including the bone morphogenetic proteins (BMP) BMP2, BMP4, BMP6, BMP7, and Activin cytokine signals and subsequently SMAD phosphorylation of SmadI, Smad5, and Smad8 (Yu et al. Nat Med. 2008. 14:1363-1369; Cuny et al. Bioorg. Med. Chem. Lett. 2008. 18: 4388-4392, herein incorporated by references). The LDN193189 presents the structure below:

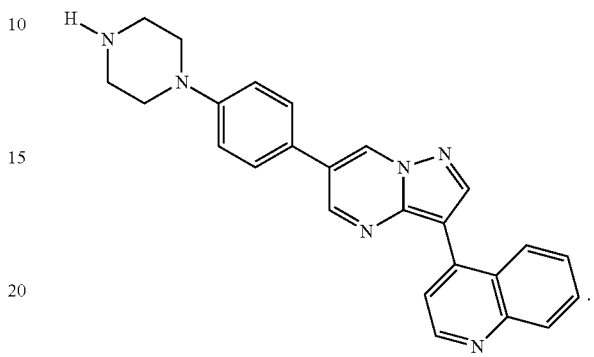

Preferred amounts of LDN193189 to be employed are between about 100 and about 700 nM, more preferably between about 150 and about 650 nM, such as for example between about 200 and about 600 nM and most preferably the amount is about 500 nM.

As used herein, the term "glycogen synthase kinase 3β inhibitor" or "GSK-3 inhibitor" or CHIR refers to a compound that inhibits a glycogen synthase kinase 3β enzyme, for example, see, Doble, et al., J Cell Sci. 2003; 116:1175-1186, herein incorporated by reference. Specifically, CHIR99021 has a CAS number 252917-06-9, a molecular formula of $C_{22}H_{18}Cl_2N_8$, and a name of 6-(2-(4-(2,4-Dichlorophenyl)-5-(4-methyl-1H-imidazol-2-yl)-pyrimidin-2-ylamino)ethyl-amino)-nicotinonitrile, for example, see structure below:

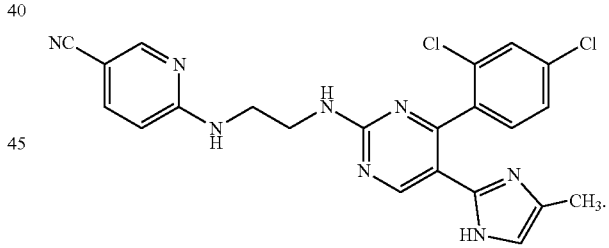

Preferred amounts of CHIR99021 to be employed are between about 0.1 and about 10 μM, more preferably between about 1 and about 7 μM, such as for example between about 5 and about 6 μM and most preferably the amount is about 3 μM.

The term "mitogens", as used herein, refers to those compounds that are members of the family of fibroblast growth factors, such as FGF-2 (basic FGF), and FGF-4. Also exemplary is epidermal growth factor (EGF), functional homologs, and other factors that bind the EGF receptor. Other candidate growth factors are platelet-derived growth factor (PDGF), insulin-like growth factor (IGF). These mitogens are used for increasing the number of a lineage cells, causing them to proliferate further in a culture.

Neurotrophic factors are endogenous peptides, found in the nervous system or in non-nerve tissues innervated by the nervous system, that function to promote the survival and maintain the phenotypic differentiation of nerve and/or glial cells. The family of trophic factors, called the neurotrophins, currently includes brain-derived neurotrophic factor (BDNF), nerve growth factor (NGF), glial cell line-derived neurotrophic factor (GDNF), neurotrophin-3 (NT-3), NT-4/5, and NT-6. All neurotrophic factors can be used isolated or in combination.

Preferred amounts of each neurotrophic factor to be employed is between about 1 ng/mL and about 25 ng/mL, more preferably between about 5 ng/mL and about 15 ng/mL, more preferably about 10 ng/mL.

As used herein, the expression "differentiation inductor", refers to the ascorbic acid (AA).

Preferred amounts of the differentiation inductor to be employed is between about 50 µM and about 500 µM, more preferably between about 100 µM and about 300 µM, more preferably about 200 µM.

As used herein, the expression "cell transduction inductor" refers to a compound, which mediates signal transduction, such as, for example cAMP.

Preferred amounts of the cell transduction inductor to be employed is between about 0.01 mM and about 1 mM, more preferably between about 0.1 mM and about 0.8 mM, more preferably about 0.5 mM.

"Markers", as used herein, are nucleic acid or polypeptide molecules that are differentially expressed in a cell of interest. In this context, differential expression means an increased level for a positive marker and a decreased level for a negative marker as compared to an undifferentiated cell. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker or "positive" when the specific marker is sufficiently detected in the cell. Similarly, the cell is "negative for" a specific marker, or "negative" when the specific marker is not sufficiently detected in the cell.

As used herein, the term "activator" "activating" refers to compounds for activating molecules resulting in directed differentiation of cells of the present invention. Exemplary activators include but are not limited to: noxious heat/cold, mechanical stimulation, chemical stimuli (menthol, piperine, acute capsaicin, cinnamaldehyde, resiniferatoxin, bradykinin, ATP, prostaglandins, inflammatory cytokines, acidic saline, fibroblast growth factor (FGF), etc).

Biological agents, as referred herein, encompass many ingredients used in topical products are known irritants or are potentially irritating, especially to people with "sensitive skin". These irritating ingredients include fragrances, preservatives, solvents, propellants and many other ingredients that might otherwise be considered inert components of the products. Additionally, many topical product active ingredients, including chemicals that may also be classified as drugs, produce irritation when applied to the skin. These include, but are not limited to ingredients such as exfoliants and skin cell renewal agents, anti-acne drugs, antiperspirant compounds, antihistamines, anti-inflammatory agents, skin protective agents, insect repellent chemicals, sunscreens and many others. Where more than one chemical irritant is present, their irritating effects may be additive. Furthermore, chemical ingredients may react with one another, or in the environment of the skin, to form new chemicals which are irritating. The vehicles in which the active drug ingredients are formulated may also produce irritation in sensitive people, especially in the case of drugs such as topical corticosteroids.

In addition to chemicals which directly trigger skin irritation, some chemicals indirectly cause the skin to become more sensitive to other chemicals or environmental conditions which would not normally cause irritation. Many chemicals which act as skin "exfoliants" such as retinoids (e.g. tretinoin, retinol and retinal), carboxylic acids including α-hydroxy acids (e.g. lactic acid, glycolic acid), p-hydroxy acids (e.g. salicylic acid), α-keto acids, acetic acid and trichloroacetic acid, 1-pyrrolidone-5-carboxylic acid, caprylyl salicylic acid, α-hydroxy decanoic acid, α-hydroxy octanoic acid, gluconolactone, methoxypropyl gluconamide, oxalic acid, malic acid, tartaric acid, mandelic acid, benzylic acid, gluconic acid, benzoyl peroxide and phenol, among others, may cause the skin to become more sensitive to irritation triggered by other topically-applied chemicals such as moisturizers, sunscreens, fragrances, preservatives, surfactants (e.g. soaps, shaving cream) and other topical products.

The irritants cited above, can also be tested in the PSN cell culture of the present invention, since it could be used as an in vitro model for skin sensibility, neurogenic inflammation and skin sensitization.

As referred herein, TRP (transient receptor potential) channels comprehend a diverse family of ligand-gated, mostly non-selective, cation channels that are robustly expressed in sensory systems throughout species (Nilius & Szallasi, Transient receptor potential channels as drug targets from the science of basic research to the art of medicine. Pharmacol Rev 2014; 66(3): 676-814). Of these, TRPV1 is the most well studied and considered the prototypical TRP channel present in somatosensory neurons (Basbaum et al., Cellular and molecular mechanisms of pain. Cell.; 2009; 139:267-284,). TRPV1 can be directly gated by external molecules such as capsaicin, resiniferatoxin and piperine, and also modulated positively or negatively via activation of other receptors and second messenger systems, such as PIP2 hydrolysis and PKC phosphorylation (Julius, TRP channels and pain. Annu Rev Cell Dev Biol. 2013; 29:355-84). One of the receptors that seem to inhibit TRPV1 activation is the cannabinoid 1 receptor (CB1), also present in somatosensory neurons (Julius & Basbaum, Molecular mechanisms of nociception. Nature. 2001; 413:203-210). However, an endogenous agonist of CB1, anandamide, is also an agonist of TRPV1, albeit with a EC50 an order of magnitude higher in the latter (Zygmunt et al., Vanilloid receptors on sensory nerves mediate the vasodilator action of anandamide. Nature. 1999; 400:452-457).

Keratinocytes and sensory neurons have an extensive interplay during development and within the mature skin. For instance, keratinocytes release neurotrophic factors that induce arborization of free nerve endings and neurite outgrowth toward the skin surface (Albers & Davis, The skin as a neurotrophic organ. Neuroscientist. 2007; 13:371-82). They also release inflammatory mediators involved in responses to tissue damage and hypersensitivity reactions, as well as responses to cold and heat, through receptors of the TRP family of cation channels (Chung et al., TRPV3 and TRPV4 mediate warmth-evoked currents in primary mouse keratinocytes. J Biol Chem. 2004; 279:21569-75). On the other hand, sensory endings do not only transduce sensory signals, but have an active role in the cutaneous metabolism and homeostasis, through the secretion of pro-inflammatory neuropeptides and inflammatory mediators that control vascularization and tissue renewal (Roosterman et al., Neuronal control of skin function: the skin as a neuroimmunoendocrine organ. Physiol Rev. 2006; 86:1309-79). Particularly, TRPV1 positive nociceptors also regulate skin longevity and metabolism, as well as the immune response over aging (Riera et al., TRPV1 pain receptors regulate longevity and metabolism by neuropeptide signaling. Cell 2014; 157, 1023-1036).

Substance P (SP) is a neuropeptide member of the tachykinin family, synthesized by sensory neurons that emit their extensions from the DRG to the more superficial layers of the skin, mediating the communication between peripheral neurons and epidermal keratinocytes (Ribeiro-da-Silva & Hokfelt, Neuroanatomical localization of Substance P in the CNS and sensory neurons. Neuropeptides. 2000; 34:256-271). Most of the neurons that release substance P are sensitive to capsaicin, highlighting the importance of TRPV1 expression and sensory neurons-keratinocytes interplay.

EXAMPLES

Differentiation of Human Induced Pluripotent Stem Cells (hiPSCs) to NCPCs

Human induced pluripotent stem cells (hiPSC) were cultured in mTeSR™1 medium (STEMCELL Technologies, Canada) on Matrigel (BD Biosciences)-coated dishes in standard culture conditions (37° C., 5% $CO_2$). The colonies were split using 0.5 mM EDTA (Thermo Fisher Scientific, USA) every 4-5 days. Human iPS cell cultures at 40-70% confluence were used for NCPC induction. hiPSCs were exposed for 10 days (see the FIG. 1) to chemically defined 3N induction medium (DMEM+Neurobasal medium 50:50 v/v, 1% Glutamax, 0.5% N2, 1% B27, 0.5% NEAA, 55 mM β-mercaptoethanol and 1% Penicillin/Streptomycin, all from Thermo Fisher Scientific, USA) freshly supplemented with three small-molecule compounds. The addition of these compounds was as following: day 1:500 nM LDN (Stemgen, USA)+10 μM SB (Sigma Aldrich, USA); day 2: 500 nM LDN+10 μM SB+3 μM CHIR (Tocris Bioscience, USA); day 3: 10 μM SB+3 μM CHIR. At days 4, 6 and 8, the medium was supplemented only with 3 μM CHIR. After 10 days of differentiation, NCPCs were further cultured in expansion medium (3N medium freshly supplemented with 10 ng/mL bFGF and 10 ng/mL EGF, both from Thermo Fisher Scientific, USA). At day 11, NCPCs were enzymatically passaged (passage 0) using Accutase (Merck Millipore, USA) for 2-3 min at 37° C. and split 1:3 onto Poly-L-ornithine (100 ug/mL, Sigma Aldrich, USA)/Laminine (20 μg/mL, Thermo Fisher Scientific, USA)-coated dishes and cultured until confluent. The medium was replaced every other day. When 70-100% confluence was reached (normally 24-48 h after passage 0), the cells were passaged again and cultured in a culture vessel at specific densities: $1\times10^6$ cell per 60 mm dish or $3\times10^6$ cell per 100 mm dish. 10 μM ROCK inhibitor (Merck Millipore, USA) was added at the day of passaging and removed 24 h after.

Generation of Peripheral Sensory Neurons from NCPCs

NCPC cultures at approximately 80% confluence (usually at day 13, see FIG. 1) were used for neuronal differentiation. Briefly, the cells were maintained for approximately 23 days in neural induction medium containing the following differentiation factors: 0.5 mM AMPc (Sigma Aldrich, USA), 200 μM AA (Sigma Aldrich, USA), 10 ng/mL NT-3 (R&D Systems, USA), 10 ng/mL NGF (R&D Systems, USA), 10 ng/mL BDNF (R&D Systems, USA) and 10 ng/mL GDNF (R&D Systems, USA). The medium was replaced every 3-4 days. The neurons were enzymatically split (if necessary) using Accutase (Merck Millipore, USA) for 3-5 min at 37° C. onto freshly prepared Poly-Lornithine/Laminine dishes. The addition of 10 μM ROCK inhibitor (Merck Millipore, USA) was applied at every passage to increase the survival and attachment ability of the neurons. At day 35, approximately, they neurons were harvested and cultured in a culture vessel for analysis and/or further experiments.

Human Epidermal Keratinocytes Culture

Neonatal human epidermal keratinocytes (HEKn) were obtained from Cascade Biologics (Portland, OR) and cultured in EpiLife serum-free medium (ThermoFischer). Cells were cultured in a culture vessel at 10,000 cell per well. Culture vessels previously treated with gelatin (Sigma) and medium EpiLife (Thermo Fisher Scientific) split when 70% to 75% confluence 48 h conditioning and then it was collected added fresh to the neurons medium was centrifuged to get rid of debris and dead cells.

Co-Culture of Human Peripheral Sensory Neurons and Human Epidermal Keratinocytes and Treatment with Conditioned Media On day 35 of neural differentiation, peripheral sensory neurons were harvested and cultured in a culture vessel at 30,000 cell per well onto 96-well (Perkin-Elmer, USA) Poly-L-ornithine/Laminine-coated culture vessels for additional two, five and ten days under following conditions: in co-culture with HEKn cells in standard neural induction medium; and without HEKn cells but with addition of HEKn-conditioned medium at three different proportions (25, 50 and 75%). Conditioned media were exchanged every 3 days.

Differentiation and Activity Tests

1. Immunocytochemistry

NCPCs and sensory neurons were cultured in 96-well culture vessels and fixed with 4% paraformaldehyde, permeabilized with Triton X-100 and blocked with 3% bovine serum albumin (BSA). Cells were incubated for 2 hours with primary antibodies diluted in 3% BSA. After washing with PBS, conjugated secondary antibodies were added for 40 minutes in the dark, washed thoroughly with PBS followed by a 5-minute incubation with DAPI (4',6-diamidino-2-phenylindole) for nuclear staining. After rinsing with PBS and water, 50 μl of glycerol was added as mounting media and the culture vessels were sealed with aluminum sticker before analysis. The primary antibodies used were: nestin (1:100, Sigma-Aldrich, USA), anti-beta-tubulin Class III (1:200, Merck-Millipore, Germany), anti-Islet1 (1:1000, Abcam), anti-TRPV1 (1:1000, Abcam), anti-Brn3A (1:250, Abcam) and anti-peripherin (1:250, Santa Cruz Biotechnology). Secondary antibodies conjugated with Alexa Fluor 488 and Alexa Fluor 594 (1:400, Life Technologies, USA) were incubated for 40 minutes protected from light. Nuclei were stained with 0.5 μg/mL 4'-6-diamino-2-phenylindole (DAPI) for 5 min. Images were acquired using a High-Content Screening microscope, Operetta (PerkinElmer, USA) and analysis were performed using high-content image analysis software Harmony 5.1 (PerkinElmer, USA). To identify whether NCPCs were committed to sensory neuronal fate, a double stain with Islet-1/2 and Brn3 was performed. Double stain for peripherin and Brn3 was used to quantify peripheral sensory neurons maturation level of sensory neurons, compared to immature neural-progenitors cells.

2. Calcium Assays

Neurons were cultured in a culture vessel onto PLO and Laminin-treated coverslips (where they were treated with HEKn conditioned medium for 10 days. On the day of the experiment, the medium was removed and cells were incubated with fresh medium (without factors) containing 5 μM Fura-2 AM (Molecular Probes) and 0.04% pluronic acid for one hour at 37° C. Then this solution was replaced with fluorimetry buffer, composed of (in mM): 145 NaCl, 5 KCl, 1.2 NaHPO$_4$, 1.5 CaCl$_2$, 10 D-glucose, 5 HEPES pH 7.4. If an antagonist was used, it was added to this solution at this time. After 30 minutes at 37° C., the coverslips were taken to an inverted microscope (Nikon) equipped with a CCD Camera (Orca, Hamamatsu Photonics) and Lambda DG-4 light source (Sutter Instrument). The images were acquired every 500 milliseconds via MetaFluor software (Molecular Probes) and the levels of fluorescence were represented in pseudo-color. All drugs were prepared freshly from stocks and diluted in the fluorimetry buffer, with the control stimulation containing the vehicle (0.1% ethanol).

3. ELISA

Substance P (SP) levels were determined using a commercially available ELISA kit (Cayman), following the manufacturer's instructions. Sensory neurons were cultured in a culture vessel in 24-well culture vessels at high confluence. After 24 h, cells were rinsed with fluorimetry buffer and incubated with different concentrations of agonists of TRPV1 for 45 minutes in the same buffer. When an antagonist was used, it was applied 15 minutes before, then the solution was changed to agonist plus antagonist. Subsequently, the supernatants were collected and immediately used with the ELISA kit. All experiments were performed in triplicate and absorbance levels were measured in a microculture vessel reader.

Figure 2:
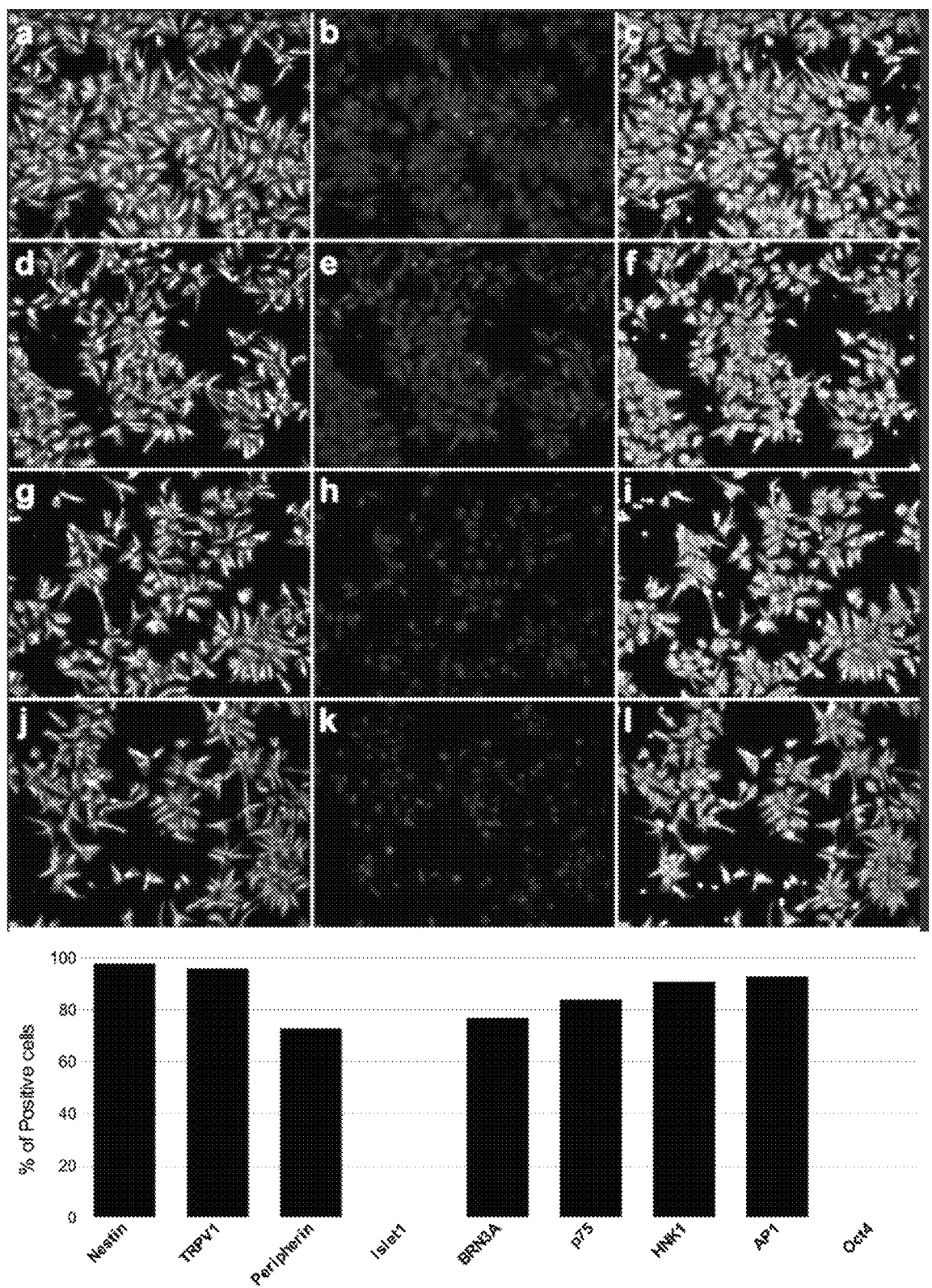
FIG. 2 shows the characterization of NCPC with specific markers. On day 10, cells presented neural progenitor cell's morphology and positive staining for Nestin (a, d, g and j), TRPV1 (b), Peripherin (e), Pax6 (h), and BRN3a (k). NCPCs were negative for Islet1 and Oct4. Nuclei were stained with DAPI (c, f, l and I). Quantification of positive cells relative to DAPI (4',6-diamidino-2-phenylindole) stained nuclei (m).

Results hiPSCs were differentiated into neural crest progenitor cells (NCPCs) via treatment with Smad inhibitors during 10 days, when NCPCs were obtained (D10, FIG. 1). After that, cells were dissociated, cultured in 96-well plates and characterized for the expression of NCPCs markers. NCPCs were positive for Nestin (FIGS. 2*a, d, g* and *j*), TRPV1 (FIG. 2*b*), Peripherin (FIG. 2*e*), Pax6 (FIG. 2*h*) and BRN3a (FIG. 2*k*) and negative for Islet1.

On day 10, NCPCs were switched to medium containing FGF and EGF for 2 days, after which they were plated onto PLO/Laminin-coated plates. Then cells were maintained in 3N medium with addition of BDNF, ascorbic acid, GDNF, NGF, NT-3 and cAMP, resulting in the formation of peripheral sensory neurons. Of note, the neurons tended to form ganglion-like structures after 7 days in 3N medium, which is also described for mouse and rat primary cultures. On day 33 (D33) of differentiation, cells were enzymatically detached and recultured on 96-well plates.

Figure 3:
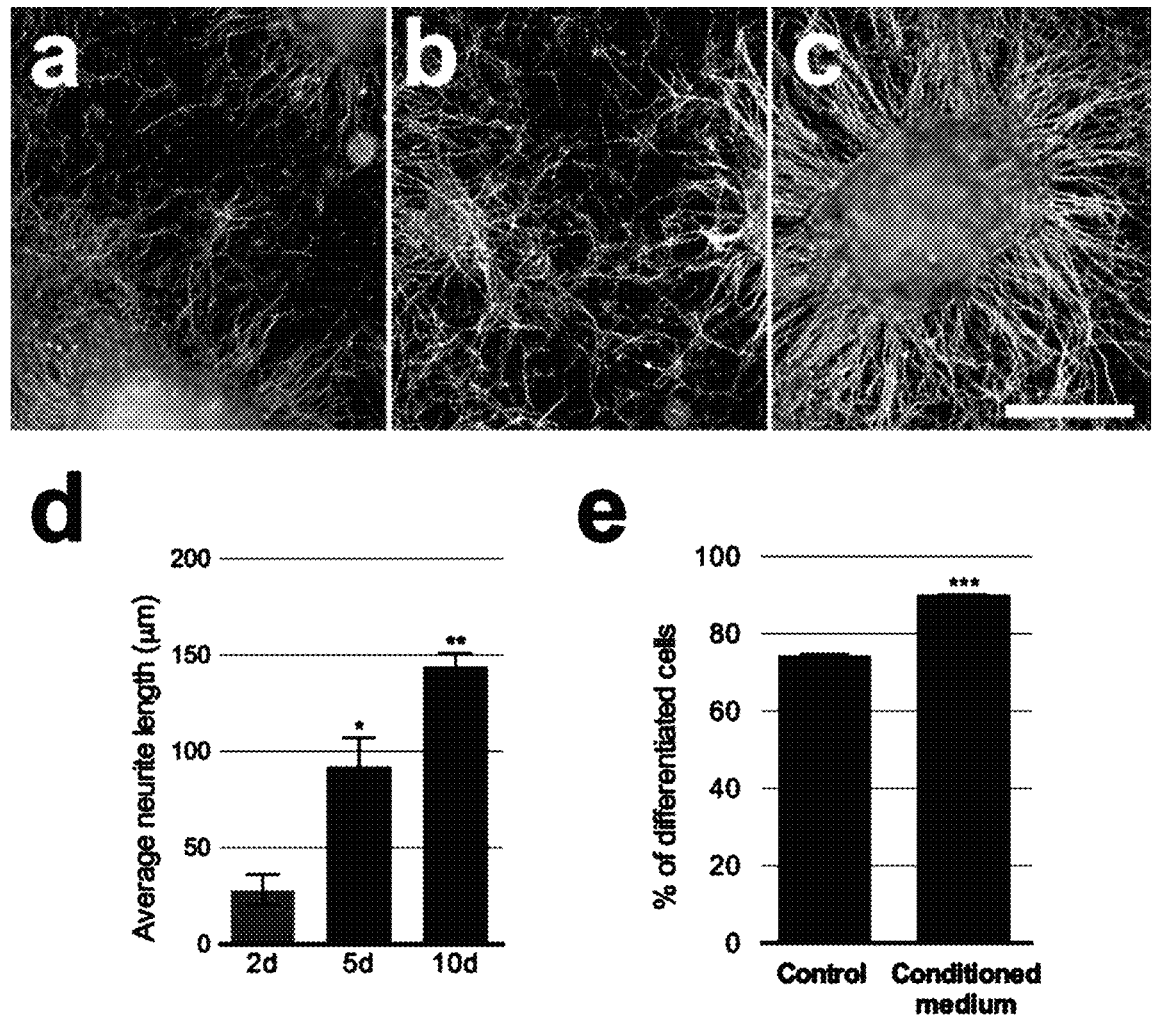
FIG. 3 shows sensory neurons differentiation. β-tubulin class III (green) stained neurons after 2, 5 or 10 days in neuronal medium conditioned with 75% HEKn medium. Nuclei were stained with DAPI (a-c). Quantification of neurite length in peripheral sensory neurons. Neurite length was measured based on β-tubulin Class III (green) immunostaining. Computer assisted image segmentation identified all neurites and measured the total length at each time point. Neurites increased 328% in length after 5 days and 514% after 10 days in culture with 75% HEKn conditioned medium (d). Percentage of differentiated neurons. HEKn cells conditioned medium increased 17.4% the number of neurons after 10 days of culturing (e).

The immature peripheral sensory neurons were treated with HEKn-conditioned medium. HEKn-conditioned medium was mixed with 3N medium at 75%, and added to the neurons for 2, 5 and 10 days. Then it was quantified the neuronal maturation with βTubulin III staining at these different time points. The neurites emanating from the ganglion-like structures increased robustly over this time, approximately 157% in length after 5 days in culture and 542% after 10 days (FIGS. 3*a, b, c* and *d*). The presence of HEKn conditioned medium accounts for a 17.4% increase in the differentiation of these cells when compared to control cultures (FIG. 3*e*).

Figure 4:
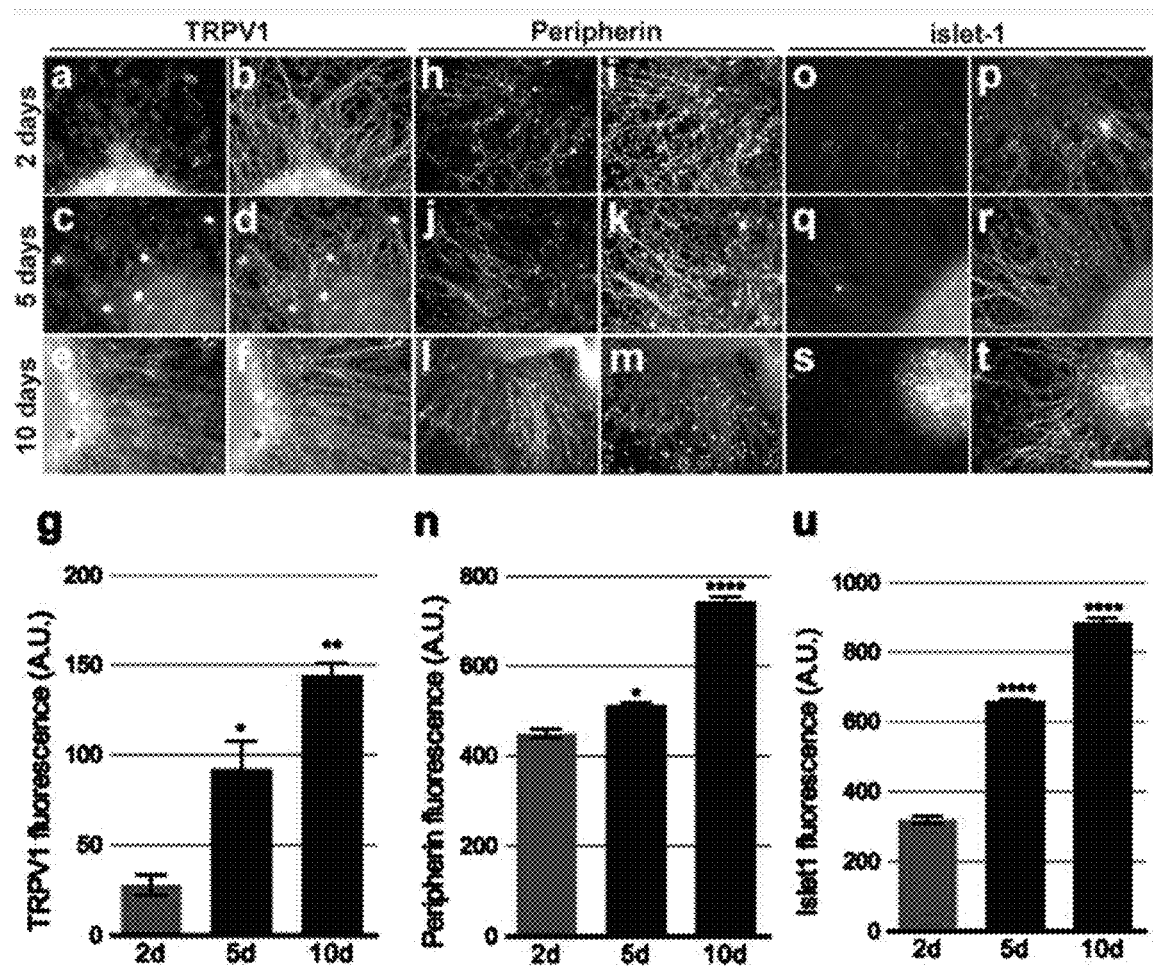
FIG. 4 show peripheral sensory neurons maturation. Neurons cultivated in 75% HEKn cells media presented time related increasing expression of TRPV1 (a, c and e), Peripherin (h, j and l) and Islet-1 (o, q and s). β-tubulin class III (green) and DAPI were co-stained in all conditions (b, d, f, I, k, m, p, r and t). TRPV1 fluorescence intensity increased 328% and 514% after 5 and 10 days respectively (g); Peripherin showed 118% and 165% increase after 5 and 10 days respectively (n) and Islet-1 also presented 205% and 276% increase after 5 and 10 days respectively (u).

There are several markers that make up the distinctive expression profile of somatosensory neurons. It was evaluated the expression of TRPV1 (FIG. 4*a-g*), Peripherin (PRPH, FIG. 4*h-n*) and Islet 1 (FIG. 4*o-u*). All markers had increased expression at the time points observed (FIGS. 4*g, n* and *u*). These results shows that conditioned medium promoted maturation and growth of sensory neurons, as they exhibited higher expression of differentiation markers, hallmarks of the transition into sensory neurons maturity.

Figure 5:
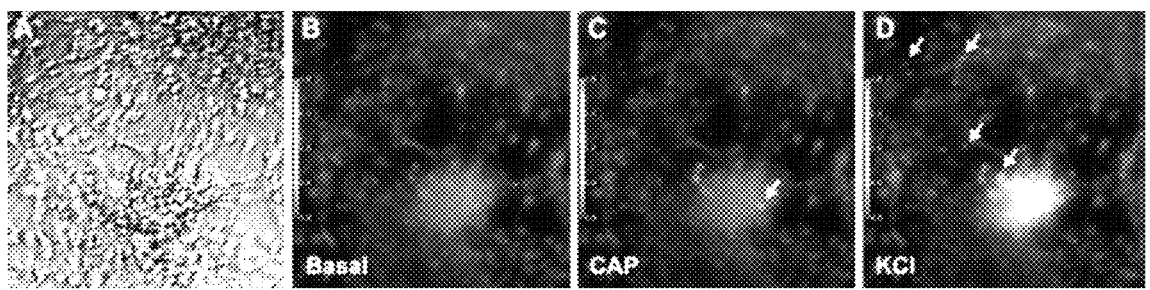
FIG. 5 shows the calcium release assay in hiPS cells derived sensory neurons. Phase contrast image for cell localization (a) fluorescence image of basal calcium levels (b). Calcium responses in sensory neurons after 100 nM capsaicin (c) and 70 mM KCL treatment (d). Calcium imaging of sensory neurons with conversion of Fura-2 excitation ratio (340/380 nm) to pseudo color, according to the scale on the left of each image. Arrows indicate active cells.

The TRPV1 channel is a non-selective cation-permeable channel, with significant calcium permeability (Szallazi et al., The vanilloid receptor TRPV1: 10 years from channel cloning to antagonist proof-of-concept. Nat Rev Drug Discov, 2007; 6: 357-372). For this reason, intracellular calcium measurements have been used as a proxy to TRPV1 activation. It was quantified the calcium increases mediated by TRPV1 activation by obtaining dynamic images of calcium transients in individual cells. In these experiments, Capsaicin-induced activity could be detected (FIG. 5).

Figure 6:
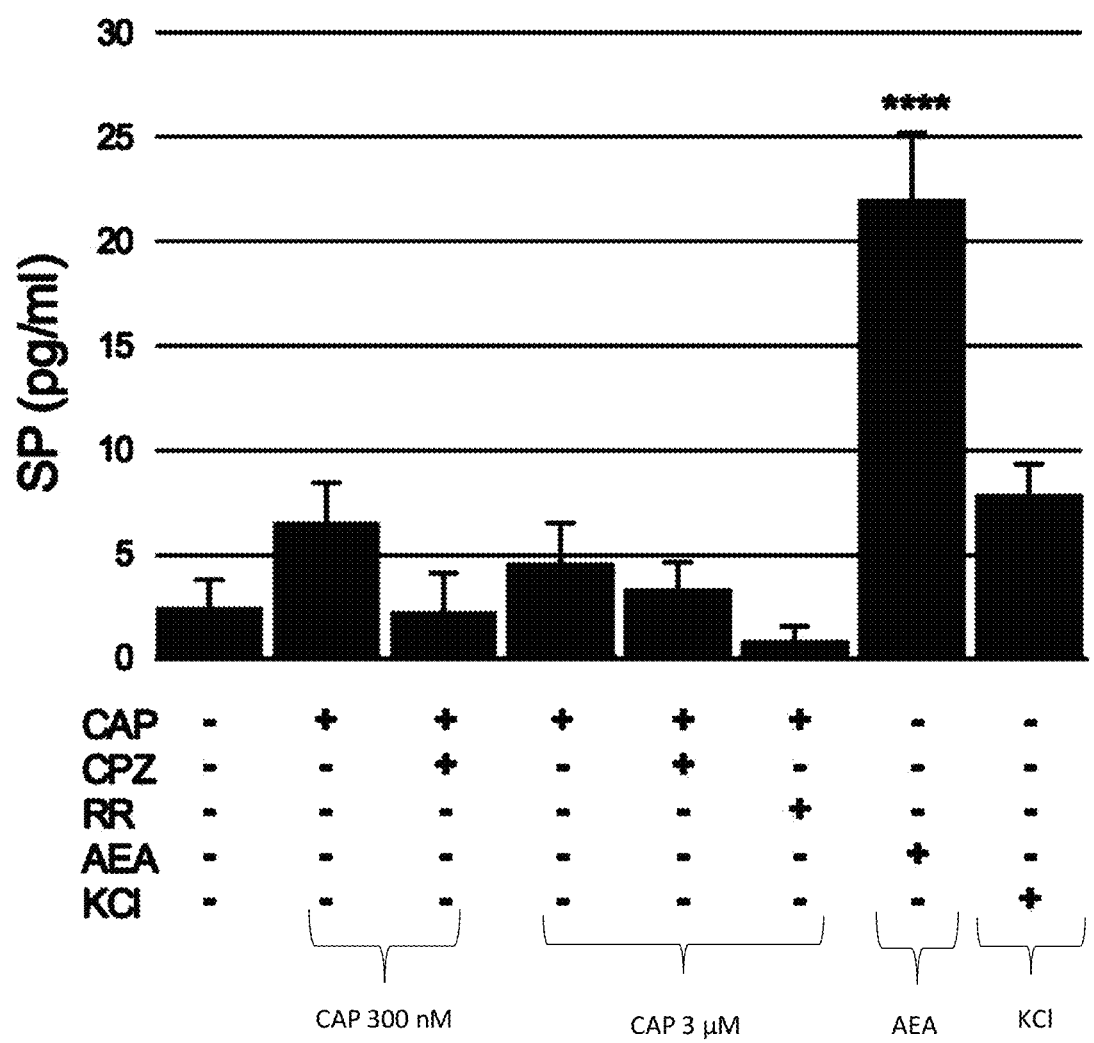
FIG. 6 shows substance P release after in vitro treatment with agonists and antagonists. Substance P release measured in the supernatant of sensory neurons culture after incubating 1 h at 37° C. in the presence of ligands. CAP: capsaicin; CPZ: capsazepine; RR: ruthenium red; AEA: anandamide (10 μM); KCl: high potassium solution (70 mM). AEA presented 887% increase compared to control.

PSNs respond to irritants, such as capsaicin, via release of neuropeptides at the epidermal end and glutamate and neuropeptides in the dorsal horn of the medulla (Basbaum et al., Cellular and molecular mechanisms of pain. Cell. 2009; 139:267-284). To verify if the sensory neurons were functional with respect to neuropeptide release, after D33 they were plated onto 24-well plates and treated 10 days with HEKn conditioned medium. Substance P presented a basal level of approximately 3 μg/ml/h. Capsaicin at 300 nM was able to triple that amount, albeit non statistically significant. This increase was efficiently blocked by the co-treatment with capsazepine at 1 μM. A higher concentration of capsaicin was applied (3 μM), but did not show increased release, probably due to TRPV1 desensitization. Pre-incubation with ruthenium red (10 μM) followed by capsaicin (3 μM) seemed to decrease substance P release below basal levels. Interestingly, anandamide (10 μM) evoked the highest substance P release with these cells. Finally, when a high potassium solution (70 mM) was added to depolarize neurons, it was obtained substance P release equivalent to capsaicin 300 r1M (FIG. 6).

It is showed in the present invention, the important TRPV1 activity, the release of SP mediated by capsaicin and anandamide in the cell culture produced by the method according to the present inventions, which could be used for screening irritants and possibly analgesics.

The invention claimed is:

1. A method for inducing differentiation of human induced pluripotent stem cells to peripheral sensory neuronal (PSN) cells, comprising:

(a) the provision of:

(i) a cell culture comprising human induced pluripotent stem cells (HiPSCs);

(ii) a 3N medium;

(iii) Small Mothers Against Decapentaplegic (SMAD) pathway inhibitors LDN193189, SB431542, and CHIR;

(b) contacting said stem cells of (i) with (ii) and (iii) on a first culture vessel from 2 to 22 days in vitro to obtain primarily differentiated cells from the HiPSCs;

(c) contacting, in a second culture vessel, the primarily differentiated cells with 3N medium, supplemented with fibroblast growth factor (FGF-2) and epidermal growth factor (EGF), coated with polyornithine/laminin, wherein the primarily differentiated cells are maintained in said culture for up to 12 days;

(d) immediately following step (c), contacting the primarily differentiated cells with 3N medium, supplemented brain derived neurotrophic factor (BDNF), neurotrophin-3 (NT-3), glial cell line derived neurotrophic factor (GDNF), nerve growth factor (NGF), ascorbic acid, and cyclic adenosine monophosphate (cAMP), and maintaining the primarily differentiated cells from 5 to 25 days in culture to obtain secondary differentiated cells that are peripheral sensory neuronal (PSN) cells; and (e) culturing the secondary differentiated PSN cells from 2 to 22 days in conditioned human epidermal keratinocytes neonatal (HEKn) medium.

2. The method according to claim 1, wherein the LDN193189 is between about 100 and about 700 nM, the SB431542 is between about 0.1 and about 100 µM and the CHIR is between about 0.1 and about 10 µM.

3. The method according to claim 1, wherein the primarily differentiated cells are Neural Crest Progenitor Cells (NCPC).

4. The method according to claim 3, wherein the NCPCs express one or more markers selected from the group consisting of Nestin, TRPV1, Peripherin, Pax 6 and BRN3a.

5. The method according to claim 1, wherein the peripheral sensory neuronal cells express one or more markers selected from the group consisting of TRPV1 and Substance P.

6. A method of screening a biological agent in vitro, comprising:

(a) the provision of:
  (i) a plurality of peripheral sensory neurons derived in vitro from a method for inducing differentiation to peripheral sensory neuronal (PSN) cells, according to claim 1; and
  (ii) a test compound; and
(b) contacting said peripheral sensory neurons with said test compound and measuring a function of the peripheral sensory neurons, wherein said function is measurement of at least one marker's activity.

7. The method according to claim 6, wherein the marker is chosen from TRPV1 and Substance P.

8. The method according to claim 1, wherein the 3N medium comprises N2-containing medium and B27-containing medium.

9. The method according to claim 8, wherein the 3N medium comprises a 1:1 mixture of the N2-containing medium and the B27-containing medium.

10. The method according to claim 1, wherein the conditioned human epidermal keratinocytes neonatal (HEKn) medium comprises a neural induction medium in which HEKn cells have been cultured.

* * * * *